United States Patent [19]

Hoffman

[11] Patent Number: 5,788,499
[45] Date of Patent: Aug. 4, 1998

[54] POSTERIOR COMPOSITE RESTORATION INSTRUMENT AND METHOD

[76] Inventor: Craig A. Hoffman, 146 W. Clark St., Albert Lea, Minn. 56007

[21] Appl. No.: 723,187

[22] Filed: Sep. 27, 1996

Related U.S. Application Data

[63] Continuation-in-part of Ser. No. 570,661, Dec. 11, 1995, abandoned.
[51] Int. Cl.$^6$ ............................................. A61C 5/04
[52] U.S. Cl. ........................ 433/226; 433/149; 433/152; 433/155
[58] Field of Search ........................ 433/39, 149, 152, 433/155, 156, 163, 229, 228.1, 141

[56] References Cited

U.S. PATENT DOCUMENTS

| | | | |
|---|---|---|---|
| 2,035,347 | 3/1936 | Shotton | 32/15 |
| 2,636,269 | 4/1953 | Sweeten | 32/63 |
| 3,510,948 | 5/1970 | Walthall | 433/149 |
| 4,273,534 | 6/1981 | Seid | 433/164 X |
| 4,306,864 | 12/1981 | Law et al. | 433/164 X |
| 4,340,069 | 7/1982 | Yeaple | 433/72 X |
| 4,515,563 | 5/1985 | Dungill | 433/164 X |
| 4,608,021 | 8/1986 | Barrett | 433/229 |
| 4,634,383 | 1/1987 | Beyer et al. | 433/164 X |
| 4,673,353 | 6/1987 | Nevin | 433/90 |
| 4,778,385 | 10/1988 | Herrin | 433/40 |
| 5,030,093 | 7/1991 | Mitnick | 433/164 |
| 5,098,300 | 3/1992 | Zaki | 433/39 X |
| 5,181,755 | 1/1993 | Stanwich et al. | |
| 5,183,397 | 2/1993 | Weissman | 433/215 |

OTHER PUBLICATIONS

Richard D. Trushkowsky, DDS, FAGD, "A Panoramic Overview of Class II Posterior Resin Placement Techniques", *Dentistry Today*, Sep. 1995, pp. 60–65.

Denbur, Inc., magazine advertisement *Dentistry Today*, (this existed prior to filing).

C.E.J. Dental, magazine advertisement *Dentistry Today*, p. 29 (this existed prior to filing).

Brasseler, Inc. advertisement for Carbide Carvers (this existed prior to filing).

Pulpdent® "Single End Amalgam Carrier" package advertising for a stainless steel amalgam carrier (undated).

*Primary Examiner*—Nicholas D. Lucchesi
*Attorney, Agent, or Firm*—Merchant, Gould, Smith, Edell, Welter & Schmidt

[57] ABSTRACT

A method and apparatus for restoration of teeth using light curable restoratives while assuring interproximal contact between the restored tooth and an adjacent tooth. The apparatus is in the form of a hand-held instrument with a specialized tip to hold an amount of pre-cured composite which is made from the same material as the restorative material or other compatible material and is intended for permanent placement in the tooth during the restorative process and becomes an integral part of the restoration. A tooth cavitation opening through a vertical tooth surface about which a matrix band has been tightened is filled by alternate deposition and curing of successive layers of the light curable restorative to a level at or below the plane of maximum circumference of the tooth. The amount of pre-cured composite is placed in a layer of uncured composite on this plane and the instrument is used to apply pressure to the amount of pre-cured composite to establish interproximal contact. This layer is cured, securing the amount of pre-cured composite and deforming the matrix band outwardly for subsequent filling and curing to complete the restoration.

19 Claims, 16 Drawing Sheets

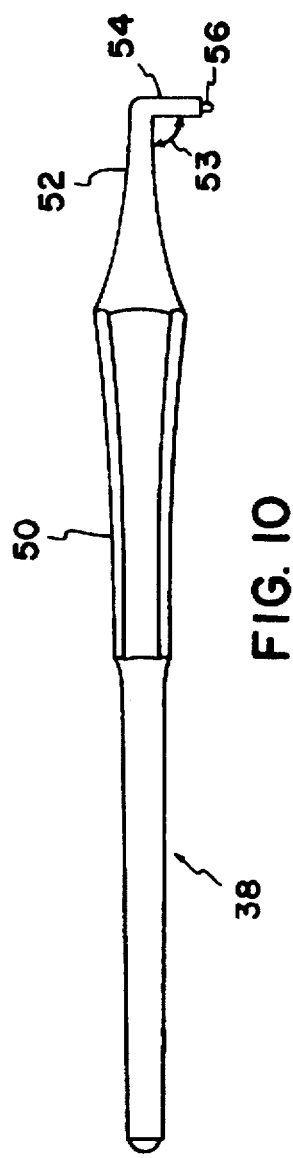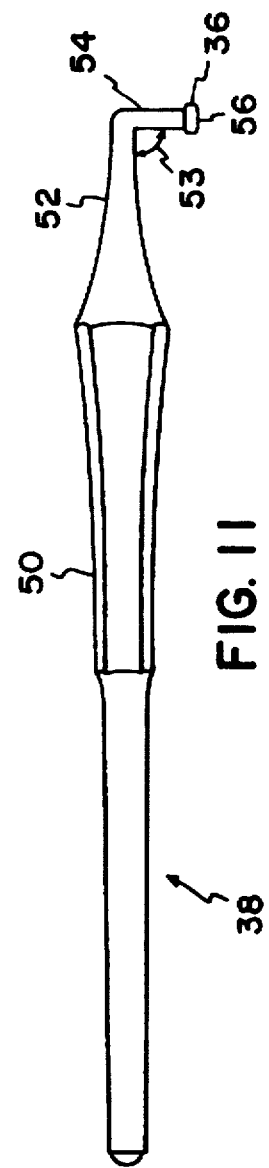
FIG. 10
FIG. 11

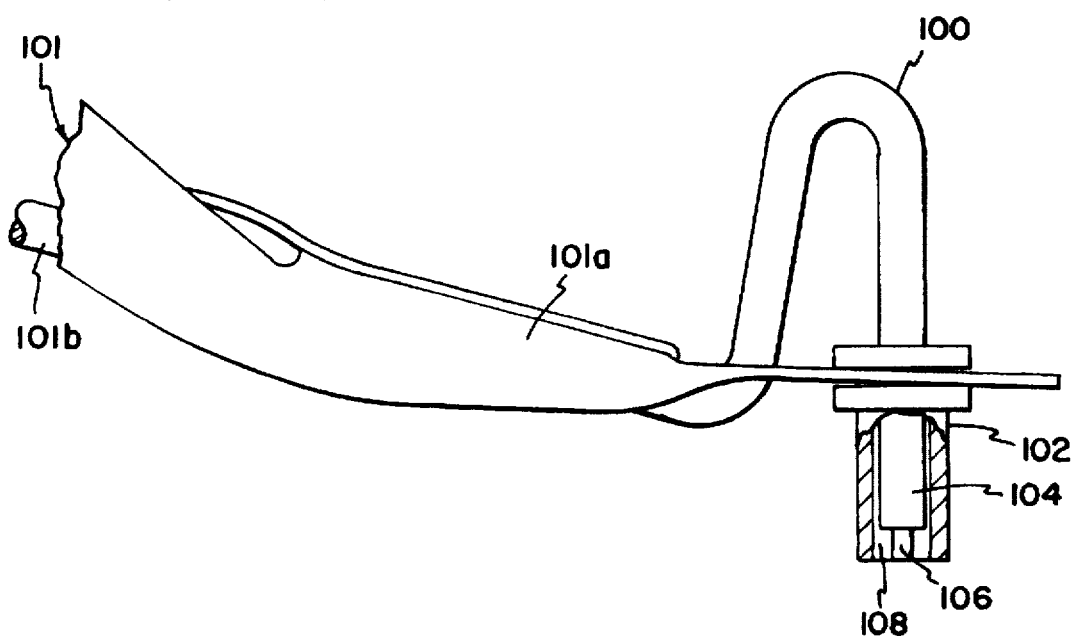
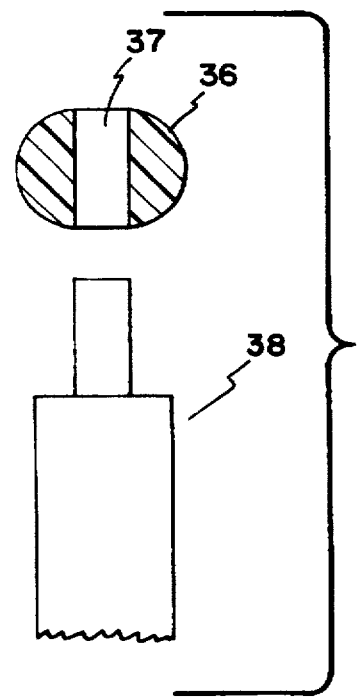
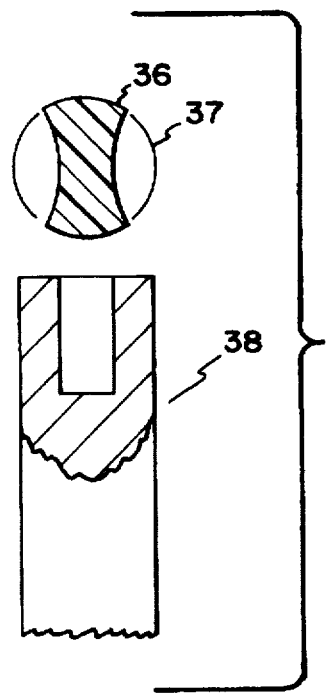

POSTERIOR COMPOSITE RESTORATION INSTRUMENT AND METHOD

This application is a Continuation-in-Part of U.S. application Ser. No. 08/570,661 filed on Dec. 11, 1995 now abandoned.

BACKGROUND

The invention disclosed here relates to the field of tooth restoration. Restoration is the filling of a void or cavity within a tooth to prevent the loss of that tooth and to restore its utility. Specifically, but not exclusively, this invention is adapted to the restoration of posterior teeth using light curable, polymeric restoratives, commonly known as composites, while providing proximal contact of the restored tooth with an adjacent tooth.

It is conventional practice in the restoration of posterior teeth to surround the vertical surfaces of the tooth with a deformable, foil-like matrix band. This matrix band forms a dam across the open vertical mouth of the cavity, which is typically through the front or rear vertical surface of the tooth. Until recently, metallic amalgams were used almost exclusively in posterior restorations because of their compactability and high viscosity, which helped to deform the matrix band outwardly to achieve proximal contact with an adjacent tooth. Proximal contact between the restored tooth and an adjacent tooth is essential for posterior teeth, both to prevent food impaction and to keep the teeth stably positioned.

A trend in dentistry today is to use more aesthetic restorations. Composites, or light curable polymeric restoratives, provide such an advantage primarily because of the conformity of such materials in color and surface texture to natural teeth enamels. With the recent development of longer wearing composite materials and improved bonding agents, potential use of these materials for posterior restorations has greatly increased.

A major difficulty in the use of light curable, resin-based restoratives, particularly in the restoration of posterior teeth or molars where interproximal contact is considered essential, is that the uncured polymeric material is in the nature of a viscous liquid or of a plastic consistency. As a result, the uncured material tends to flow around conventional compacting tools rather than to transmit the compacting force of the tool laterally against the tightened matrix band. Because the tightened matrix band establishes a chord-like dam across the vertical opening of the tooth cavity to be filled, the cured resin restorative tends to assume the same configuration as the tightened matrix band to effect a flattened interproximal surface on the restored tooth which does not make good contact with an adjacent tooth. While the light curable restorative compositions have been developed to improve their compactability, the basically plastic nature of the uncured composite falls substantially short of the measure of matrix band deformation attainable by the compaction of amalgam restoratives. In addition, the current methods and devices which are used with composites to attempt to provide proximal contact have experienced limited and unpredictable success.

Thus, there is a need for an improvement in the attainment of interproximal contact between a tooth restored with light curable composites and an adjacent tooth.

SUMMARY

The present invention is directed to an apparatus and method for successful and consistent establishment of interproximal contact between a tooth restored with light curable composites and an adjacent tooth. The apparatus comprises a hand-held interproximal contact instrument and a piece of pre-cured composite made from the same or similar material as the restorative used in the filling. The piece of pre-cured composite has an aperture or hole in it, so as to be removably receivable on the tip of the interproximal contact instrument. An embodiment of this interproximal contact instrument comprises a handle and shaft, the shaft being bent at an angle with respect to the longitudinal axis of the handle. An end portion of this shaft has a smaller cross-section than the rest of the shaft, so that the amount of pre-cured composite fits on this end.

The present invention is further directed to an apparatus comprising a hand held instrument for use in both forming the amount of pre-cured composite and applying it to restore a cavitated tooth, as discussed in the following paragraph. This instrument has a tip formed of two concentric cylinders. The first cylinder position movably inside the second cylinder. The two cylinders are positioned such that there is an amount of space between the first and second cylinders, said space is filled with an amount of uncured composite which has been cured in a known manner. When the inner first cylinder is subsequently forced out of the second cylinder, this first cylinder can be used to apply the pre-cured composite during the restoration of a cavitated tooth in a manner similar to that described below.

In using this apparatus to restore a cavitated tooth, a matrix band is place around the tooth and wedges in a conventional manner. The lower portion of the cavity may be filled with successively cured layers as is common practice. When the filling proceeds to a level near the plane of maximum circumference of the tooth, a level of uncured material is deposited near this plane. The amount of pre-cured composite is then inserted into the cavity and positioned in close contact to the matrix band, and uncured composite is contoured about the pre-cured amount. The interproximal contact instrument's tip is placed in the aperture of the pre-cured composite, and pressure is applied pressing the pre-cured composite against the matrix band, deflecting it outwardly toward an adjacent tooth. The material is then cured, securing the pre-cured composite in the filling, so that the matrix band is permanently expanded against the adjacent tooth. Finally, the tip of the interproximal contact instrument is removed. In this manner, interproximal contact is established for posterior tooth restoration using light curable polymeric restoratives.

BRIEF DESCRIPTION OF THE DRAWINGS

These and other features, aspects and advantages of the present invention will become better understood with regard to the following description, appended claims, and accompanying drawings where:

3

Figure 5:
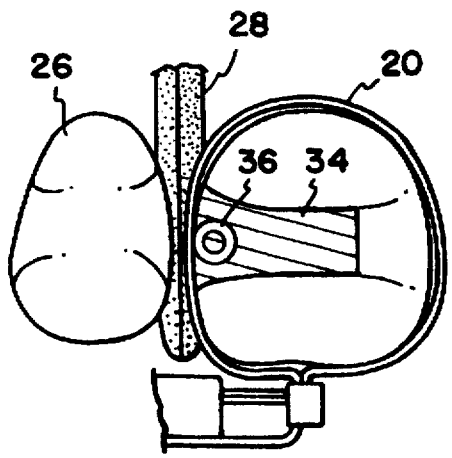
Figure 5:
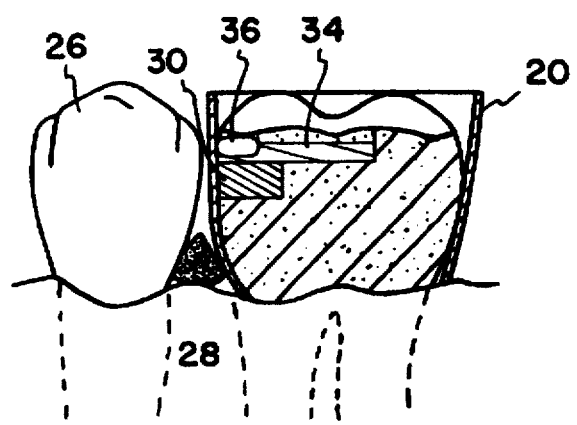
Figure 6A:
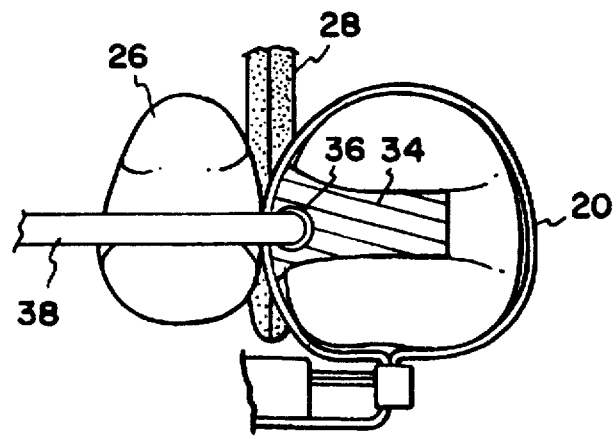
Figure 6B:
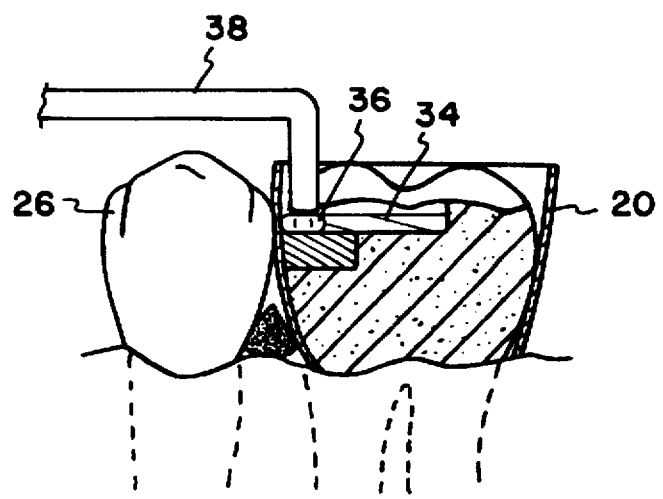
Figure 7A:
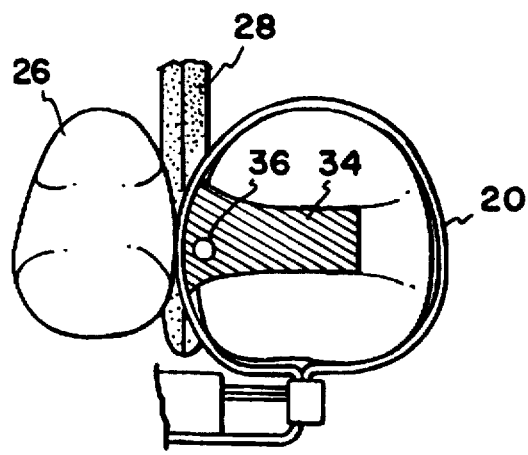
Figure 7B:
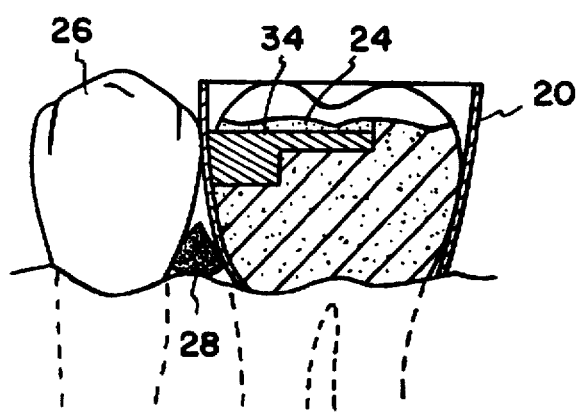
Figure 8A:
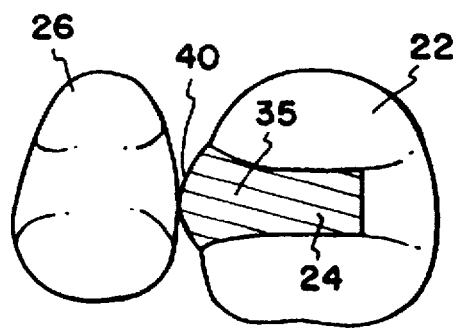
Figure 8B:
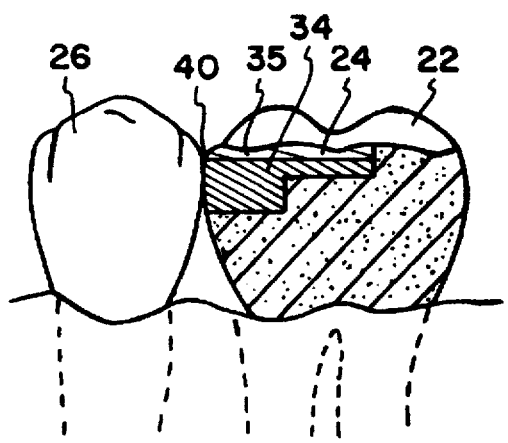
Figure 9A:
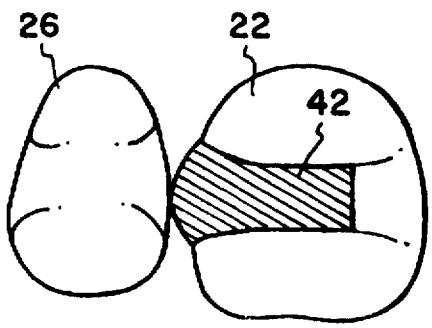
Figure 9B:
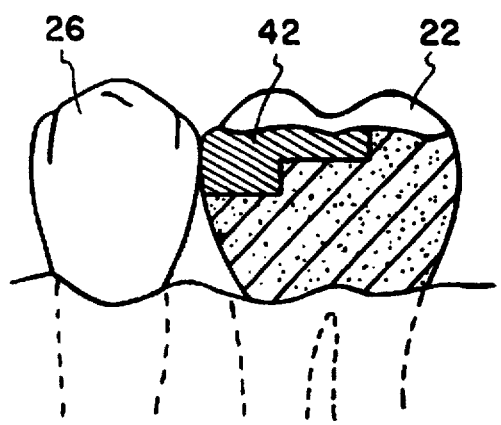
Figure 12:
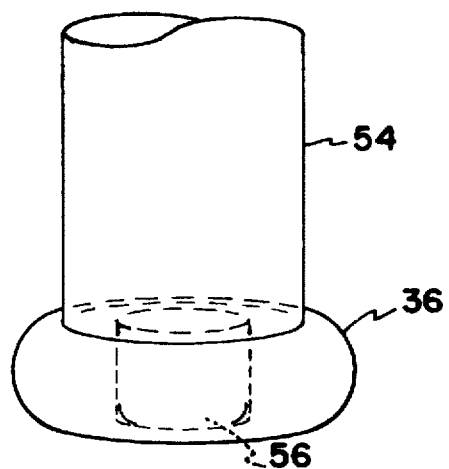
Figure 13:
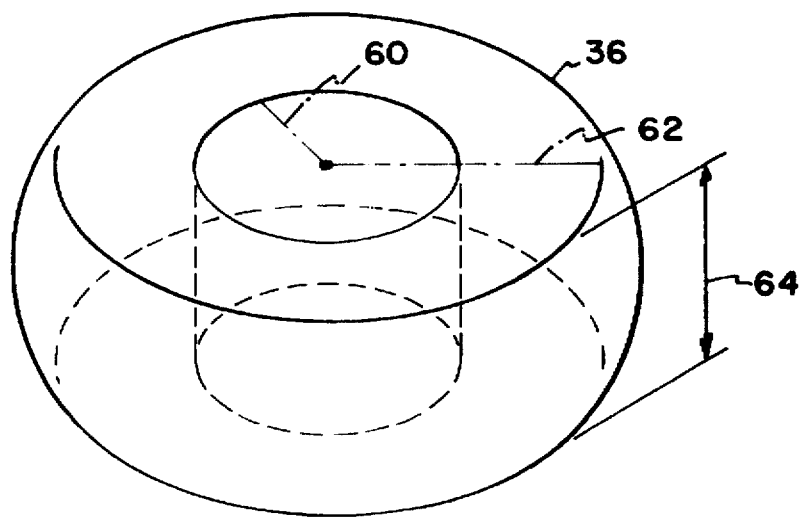
Figure 14:
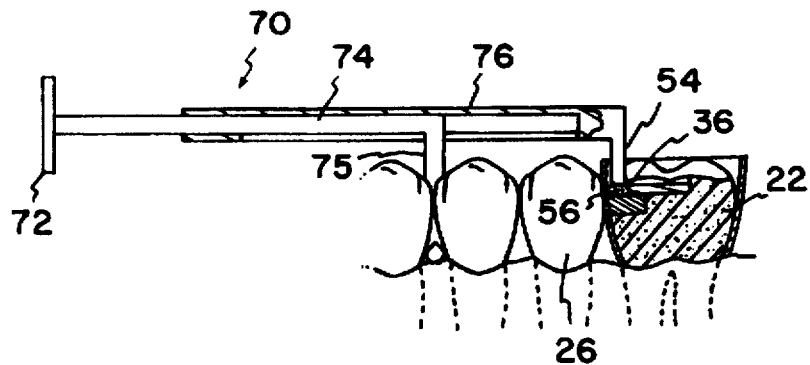
Figure 17:
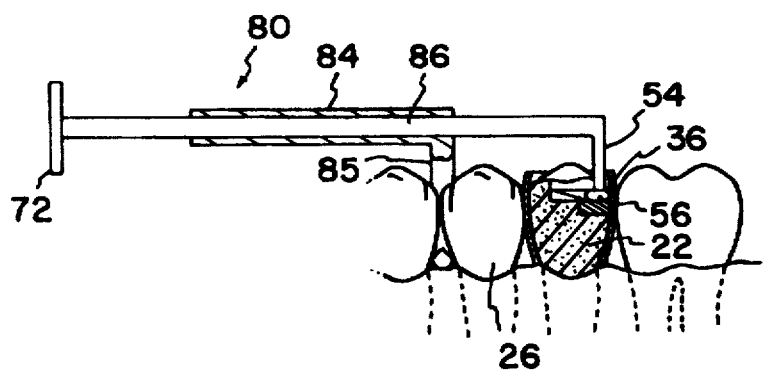
Figure 15:
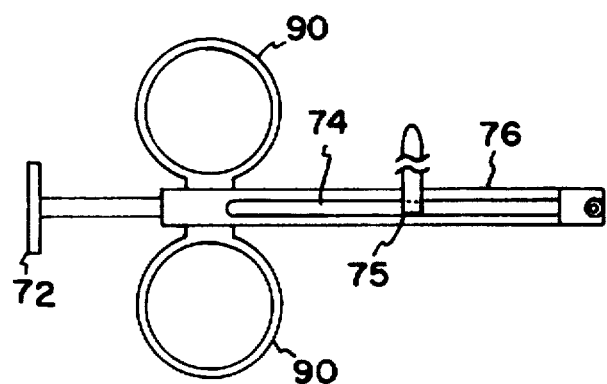
Figure 16:
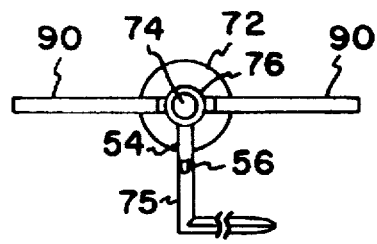
Figure 18:
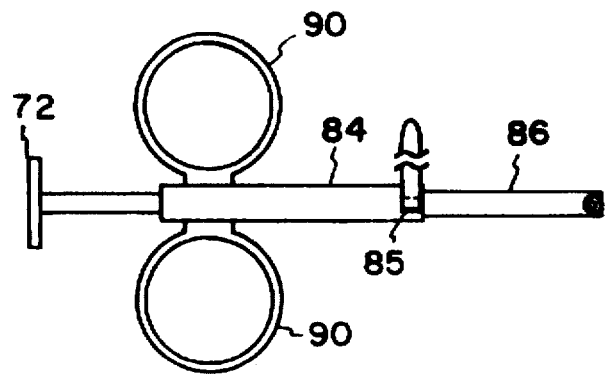

FIGS. 5A and 5B show placement of an amount of pre-cured composite with an aperture defined therein in the uncured composite;

FIGS. 6A and 6B are views showing how the interproximal contact instrument is used in conjunction with the amount of pre-cured composite to effectively deflect the matrix band outward toward the adjacent tooth to establish proximal contact;

FIGS. 7A and 7B are views showing the resulting proximal contact from FIG. 6;

FIGS. 8A and 8B show a more advanced stage of the restoration showing occlusal contour being established;

FIGS. 9A and 9B are views illustrating the completely restored tooth;

FIG. 10 shows an embodiment of the interproximal contact instrument;

FIG. 11 shows the interproximal contact instrument of FIG. 10 with the tip of the instrument inserted in the aperture of the amount of pre-cured composite;

FIG. 12 is an enlarged view of FIG. 11 showing the end of the interproximal contact instrument;

FIG. 13 is an enlarged view of an embodiment of the amount of pre-cured composite with an aperture defined therein;

FIG. 14 shows another embodiment of the interproximal contact instrument used to expand the matrix band during posterior restoration;

FIG. 15 is a top view of the instrument in FIG. 14;

FIG. 16 is a frontal view of the instrument in FIG. 14;

FIG. 17 shows another embodiment of the interproximal contact instrument used to expand the matrix band during posterior restoration;

FIG. 18 is a top view of the instrument in FIG. 17; and

Figure 19:
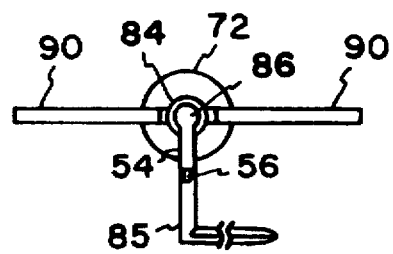

FIG. 19 is a frontal view of the instrument in FIG. 17.

Figure 21A:
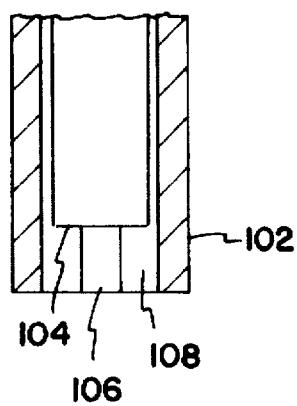
Figure 21B:
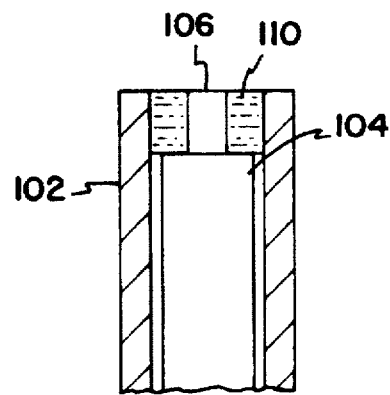
Figure 21C:
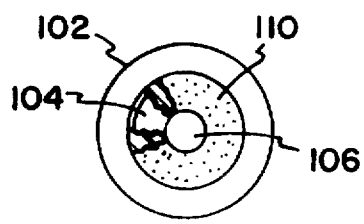
Figure 21D:
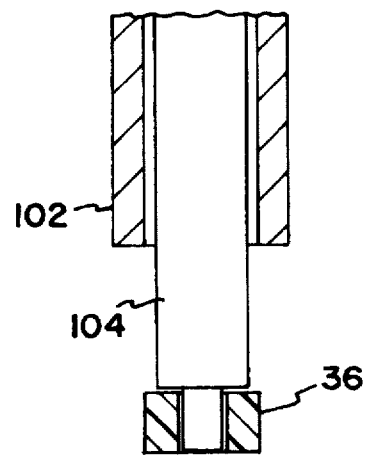

FIG. 20 shows an embodiment of an instrument used to cure the amount of pre-cured composite and to expand the matrix band during posterior restoration;

FIG. 21A shows an enlarged version of the tip of the instrument depicted in FIG. 20;

FIG. 21B shows the tip depicted in FIG. 21A inverted so as to hold an amount of uncured composite for subsequent curing;

FIG. 21C shows a top view of the tip of the instrument shown in FIG. 21B;

FIG. 21D shows the tip of the instrument depicted in FIG. 21A, with the internal cylinder forced out of the external cylinder so as to function as in interproximal contact instrument;

FIG. 22A shows another embodiment of the geometry of the amount of pre-cured composite and the tip of the interproximal contact instrument;

FIG. 22B shows another embodiment of the geometry of the amount of pre-cured composite and the tip of the interproximal contact instrument.

DETAILED DESCRIPTION

FIGS. 1–9 of the drawings illustrate successive stages of tooth restoration utilizing the present invention. FIG. 1A and 1B depicts a tooth 22 to be restored, where decayed material has been removed from the occlusal surface forming a cavitation 24. The cavitation 24, in this instance, opens through the front vertical or mesial surface of the tooth 22 which is proximal to an adjacent tooth 26. A matrix band 20 has been placed around the circumference of the cavitated tooth 22 and a wedge 28 has been place in conventional manner securing the matrix band 20 on the gingival portion of the cavitated tooth 22, and separating the cavitated tooth 22 from the adjacent tooth 26.

Figure 1A:
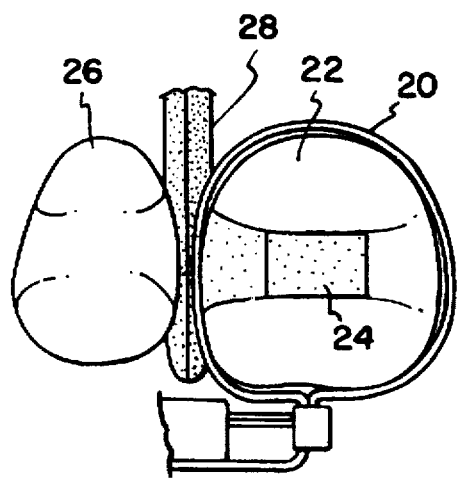
FIGS. 1A and 1B are top and side views, respectively, of a posterior tooth with decayed material removed from its proximal surface about which a matrix band has been tightened, the tooth being separated from an adjacent tooth by a wedge.
Figure 1B:
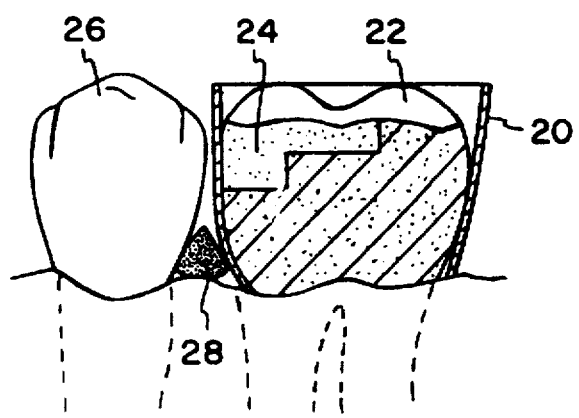
Figure 2A:
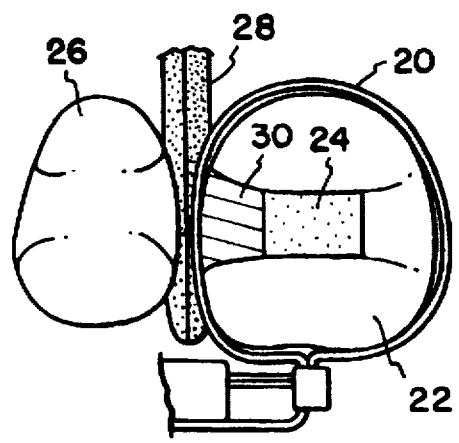
FIGS. 2A and 2B are views similar to FIGS. 1A and 1B, respectively. During initial stage of restoration, uncured composite is placed at a level near the plane of maximum peripheral dimension of the tooth to be restored.
Figure 2B:
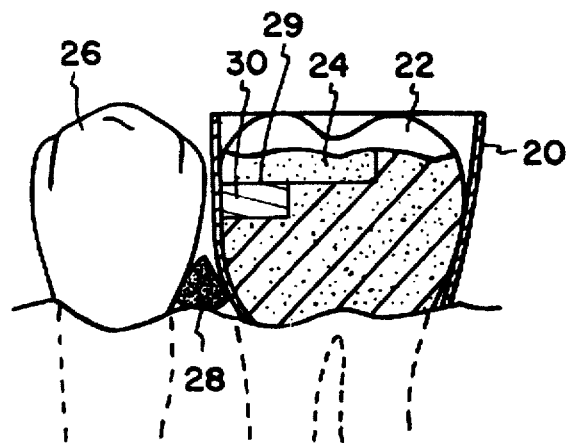
Figure 3A:
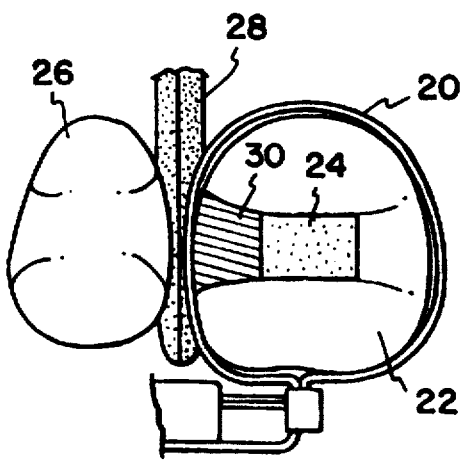
FIGS. 3A and 3B illustrate cured restorative material shown in FIGS. 2A and 2B.
Figure 3B:
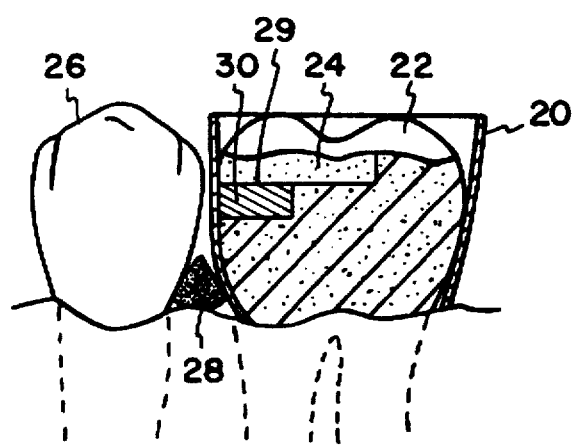
Figure 4:
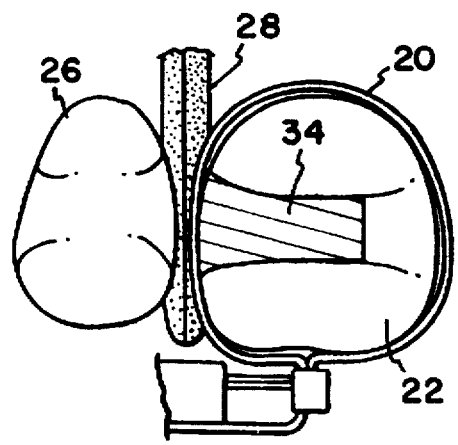
FIGS. 4A and 4B are views showing placement of uncured composite at the plane of maximum peripheral dimension.
Figure 4:
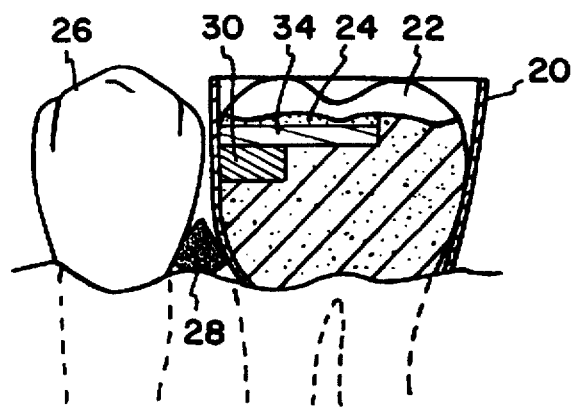

FIGS. 2A and 2B show the placement of a layer of uncured composite 30 in the lower portion of the cavitation 24. This area is filled in a conventional manner, usually in successively deposited and cured layers up to a level near but slightly below the plane of maximum peripheral dimension 29. After the composite 30 is filled and cured to this level 29, as shown in FIGS. 3A and 3B, an additional layer of uncured composite 34 is added in the cavitation 24 of the tooth 22, as illustrated in FIGS. 4A and 4B. To this uncured composite 34 an amount of pre-cured composite 36 with an aperture 37 defined therein is added, adjacent to the matrix band 20, with the aperture 37 oriented along the vertical axis of the tooth 22, as demonstrated in FIGS. 5A and 5B. The amount of pre-cured composite 36 may be constructed of the same type of restorative used for filling the cavitation 24, but is not limited to such a construction. Other suitable materials, restoratives or composites may be used to construct this amount 36.

The next step, shown in FIGS. 6A and 6B, involves the insertion of the tip of an interproximal contact instrument 38 into the aperture 37 of the amount of pre-cured composite 36. Pressure is then applied with the interproximal contact instrument 38 in such a way as to force the amount of pre-cured composite 36 against the matrix band 20, deflecting it outwardly toward the adjacent tooth 26. While pressure is being applied, the surrounding composite 34 is cured in conventional manner establishing proximal contact, shown in FIGS. 7A and 7B. The amount of pre-cured composite 36 is thus secured in the surrounding composite 34, and becomes an integral part of the restoration of the tooth 22. Additional layers of composite 35 are then added and successively cured, as shown in FIGS. 8A and 8B. Once the filling is complete, the matrix band 20 is removed, and the resulting contact point 40 between the restored tooth 22 and the adjacent tooth 26 is apparent in FIGS. 8A and 8B. FIGS. 9A and 9B show the completed restoration 42, as the entire cavitation 24 of tooth 22 is filled.

FIG. 10 shows a preferred embodiment of the interproximal contact instrument 38. The instrument 38 has a handle 50 and a shaft 52 along the same longitudinal axis. A portion of the end of the shaft 54 is bent at an angle 53 with respect to the longitudinal axis of the handle 50 and the shaft 52. Preferably, this angle 53 is between 15 and 165 degrees. More preferably, this angle 53 is between 75 and 105 degrees. Most preferably, this angle 53 is a right angle. The end portion 56 of the shaft has a cross-section which is less than the cross-section of the adjacent portion of the shaft 54. Preferably the cross-section of the shaft 52, 54, and 56 has a geometric shape such as a circle, square, rectangle, oval, or triangle. Most preferably the cross-section is circular and the shaft 52, 54, and 56 is cylindrical.

FIG. 11 shows an embodiment of the interproximal contact instrument 38 removably coupled with an amount of pre-cured composite 36. The amount of pre-cured composite 36 fits onto the end portion 56 of the shaft 54 for use in applying pressure to deform a matrix band and provide proximal contact with an adjacent tooth in the above method.

FIG. 12 is an expanded view of the amount of pre-cured composite 36 fitted on the end portion 56 of the shaft 54. Preferably the tip of the end portion 56 is rounded. The amount of pre-cured composite 36 is preferably a geometric shape with an aperture defined therein to match the geometrical shape of the cross-section of the shaft 56 of the interproximal contact instrument 38. More preferably, the amount of pre-cured composite 36 is in the shape of a cylinder with a cylindrical aperture. Most preferably, the amount of pre-cured composite 36 is in the shape of a ring.

FIG. 13 shows an embodiment of the amount of pre-cured composite 36 in the shape of a ring with a rounded, cylindrical aperture. The inner radius 60 is large enough to be removably receivable on the end portion 56 of the shaft 54 of the interproximal contact instrument 38. The outer radius 62 is slightly larger than the radius of the shaft 54 of the instrument 38. The outer radius 62 is preferably between 0.1 millimeters and 3.0 millimeters, and most preferably between 0.75 and 1.0 millimeters in length. The height 64 of the ring-shaped amount of pre-cured composite 36 is slightly more than the length of the end portion 56 of the shaft 54 of the interproximal contact instrument 38, so that said end portion 56 does not protrude out of the end of the aperture opposite the shaft 54.

FIG. 14 is another embodiment of the invention. A mesial interproximal contact instrument 70 has a handle 72, an inner shaft 74 and an outer shaft 76. The inner shaft 74 is movably received inside the outer shaft 76. The outer shaft 76 has the bent shaft 54 and the end portion 56 described above, for removably receiving the amount of pre-cured composite 36. The inner shaft 74 has an end portion 75 which is bent at an angle to the longitudinal axis of the rest of the inner shaft. This end portion 75 is preferably at an angle of 80 to 100 degrees, most preferably a right angle. The end portion 75 is placed against a tooth a number of teeth away from the tooth 22 to be restored, and provides leverage for applying pressure to the amount of pre-cured composite 36 to deform the matrix band 20 and provide proximal contact with an adjacent tooth 26.

FIG. 15 is a bottom view of the embodiment shown in FIG. 14. An alternative embodiment contains finger rings 90 used to force the outer shaft 76 in the opposite direction of the inner shaft 74 for applying pressure to the matrix band 20 described above. FIG. 16 is a frontal view of the embodiments shown in FIGS. 14 and 15.

FIG. 17 is another embodiment of the invention. A distal interproximal contact instrument 80 has a handle 72, an inner shaft 86 and an outer shaft 84. The inner shaft 86 is movably received inside the outer shaft 84. The inner shaft 86 has the bent shaft 54 and the end portion 56 described above, for removably receiving the amount of pre-cured composite 36. The outer shaft 84 has an end portion 85 which is bent at an angle to the longitudinal axis of the rest of the inner shaft. This end portion 85 is preferably at an angle of 80 to 100 degrees, most preferably a right angle. The end portion 85 is placed against a tooth a number of teeth away from the tooth 22 to be restored, and provides leverage for applying pressure to the amount of pre-cured composite 36 to deform the matrix band 20 and provide proximal contact with an adjacent tooth 26.

FIG. 18 is a bottom view of the embodiment shown in FIG. 17. This alternative embodiment contains finger rings 90 used to force the outer shaft 84 in the opposite direction of the inner shaft 86 for applying pressure to the matrix band 20 described above. FIG. 19 is a frontal view of the embodiments shown in FIGS. 17 and 18.

FIG. 20 shows a different embodiment of present invention in which an instrument 100 is used to hold the amount of composite while it is pre-cured into a specified geometry, and to place the amount of pre-cured composite into the cavitation and subsequently to expand the matrix band. The instrument 100 has an end portion that includes an inner cylindrical member 104 and an outer cylindrical member 102. The outer cylindrical member 102 functions as an outer sleeve and is slidingly mounted on the inner member 104. The instrument is preferably of the type which has a handle 101 with first and second handle portions 101a and 101b capable of pivotal movement relative to each other in a scissor-like fashion. In the preferred embodiment, the second handle portion 101b is integral with the inner cylindrical member 104 while the first handle portion 101a is connected to the outer cylindrical member 102. By forcing the handle portions 101a, b together, the outer cylindrical member 102 is retracted from the end of the inner cylindrical member 104 thereby exposing the end of the inner cylindrical member 104. An example of an instrument with the above-described type of handle is the SINGLE END AMALGAM CARRIER produced by the Pulpdent Corporation. It will be appreciated that the instrument shown in FIG. 20 has been altered in accordance with the principles of the present invention such that the inner member 104 has a distal end having a reduced diameter so as to form a small cylinder 106 on the tip. The outside barrel or sleeve has of the tool has also been shortened.

With an instrument in accordance with the principles of the present invention, the ability to make the composite ring and place it on the tip 106 of the instrument is one step. This eliminates the need for manufactured pre-cured composite rings and allows the dentist to use their choice of composites.

It will be appreciated that the length of the smaller cylinder 106 is such that, with no pressure being applied to the handle, the very end of the smaller cylinder 106 is flush with the end of the outer cylindrical member 102. This configuration creates a ring like space 108 between the outer cylindrical member 102 and the inner cylindrical member 104 and its tip 106.

FIG. 21A is an enlarged view of the end of the instrument shown in FIG. 20, displaying more clearly the features which allow this instrument to function both in curing the amount of pre-cured composite, and applying it to the cavitation. FIG. 21B illustrates the use of the instrument 100 to cure the pre-cured amount of composite. To initiate the process, uncured composite 110 is placed into the space 108 created in the end of the instrument 100.

Next, this amount of composite is cured using standard means known in the industry. FIG. 21C shows a top view of FIG. 21B, with the amount of composite 110 surrounding the smallest inner cylinder 106.

Once the amount of composite has been pre-cured, this same instrument can be used to apply the pre-cured amount of composite 36 to the cavitation, and subsequently apply pressure to the matrix band as is described above. FIG. 21D shows the inner cylindrical member 104 exposed from the outer cylindrical member 102 by applying pressure to the handle of the instrument 100. While holding the handle in this manner, the end of 104 of this instrument functions precisely as the interproximal contact instrument described previously in the specification.

As mentioned above, the amount of pre-cured composite 36 can be in various geometrical shapes. For this pre-cured composite to serve its intended purpose, its geometry need only be that of a three dimensional shape with some groove, aperture, indentation, or the like, so that an external instrument can have leverage to force said pre-cured composite 36 against the matrix band in the above described manner. FIG. 22A and FIG. 22B show two additional geometries, meant to serve as further examples, but not to limit the variety of geometries which would suit the purpose of the pre-cured composite ring.

Many modifications and variations may be made in the embodiments described herein and depicted in the accompanying drawings without departing from the concept of the present invention. Accordingly, it is clearly understood that the embodiments described and illustrated herein are illustrative only and are not intended as limitations upon the scope of the present invention.

What is claimed is:

1. An instrument used to expand a matrix band outwardly from a vertical opening of a tooth cavitation during filling of the cavitation with light curable plastic restorative compositions, said instrument comprising:
   a handle;
   a shaft extending from said handle;
   an end of said shaft opposite the handle aligned so as to form an angle with a longitudinal axis of said handle and said shaft;
   an end portion of the length of the end of said shaft having a smaller cross-section than the cross-section of said shaft; and
   an amount of pre-cured composite having an aperture defined therein, said pre-cured composite being removably receivable on the end portion of said shaft;
   whereby the amount of pre-cured composite is placed into the cavitation near the plane of maximum peripheral dimension and is surrounded by uncured composite, and the end portion of said instrument is positioned in the aperture of the pre-cured composite, and pressure applied with the instrument in an outward direction, forcing the pre-cured composite against the matrix band to establish interproximal contact with an adjacent tooth.

2. The instrument of claim 1 wherein the shaft of the instrument is cylindrical.

3. The instrument of claim 2 wherein the amount of pre-cured composite is in the shape of a ring.

4. The instrument of claim 3 wherein the aperture in the amount of pre-cured composite is cylindrical.

5. The instrument of claim 4 wherein the end portion has a length smaller than the height of the cylindrical aperture in the pre-cured composite.

6. The instrument of claim 5 wherein the end of said shaft has a smaller cross-section than the outer circumference of the cylindrical pre-cured composite.

7. The instrument of claim 1 wherein the end of the shaft opposite the handle has a rounded tip.

8. The instrument of claim 1 wherein the end of the shaft is aligned as to form a right angle with the shaft.

9. The instrument of claim 1 further comprising a second shaft movably enclosed within said shaft.

10. The instrument of claim 9 wherein the second shaft has an end aligned to form an angle with said second shaft;
    whereby the end of said second shaft is used as leverage against an adjacent tooth for applying pressure to the pre-cured composite to assist in expanding the matrix band outwardly to establish interproximal contact.

11. A method for filling a tooth cavitation with a light curable plastic composite to ensure interproximal contact with an adjacent tooth by expanding a matrix band outwardly, the method comprising the steps of;
    filling and curing composite in a lower portion of the cavitation up to a level slightly below the plane of maximum peripheral dimension of said cavitation;
    placing a layer of uncured composite near said plane of maximum peripheral dimension;
    placing an amount of pre-cured composite having an aperture into said uncured composite adjacent to the matrix band;
    applying pressure to said pre-cured composite in an outward direction toward the adjacent tooth by inserting the tip of an interproximal contact instrument into said aperture, deflecting the matrix band outwardly to establish proximal contact with the adjacent tooth;
    curing said uncured composite so that the pre-cured composite is secured in the surrounding composite; and
    filling the remaining cavitation to complete the restoration.

12. The method of claim 11 further including the step of removing the tip of the interproximal contact instrument from the pre-cured composite after curing the surrounding uncured composite, but before filling the remaining cavitation.

13. A device used in establishing interproximal contact during filling of a tooth cavitation with light curable restorative compositions, said device comprising:
    an amount of material having the following properties:
       sized to be placed into a vertical opening of the tooth cavitation during filling of the cavitation;
       constructed of pre-cured light curable restorative with the same or similar properties as the restorative composition used to fill the cavitation; and
       structured to have a three-dimensional shape with an aperture defined therein;
    whereby the amount is removably receivable on the end of an instrument so that pressure can be applied to deform a matrix band outwardly and provide interproximal contact with an adjacent tooth.

14. The device of claim 13 wherein the amount of material is in the shape of a ring.

15. The device of claim 14 wherein the aperture in the amount of material is cylindrical.

16. The device of claim 15 wherein the amount of material has an outer radius of 1.5 to 2.0 millimeters.

17. An instrument used to pre-cure an amount of composite and apply the pre-cured composite in a manner to expand a matrix band outwardly from a vertical opening of a tooth cavitation during filling of the cavitation with light curable plastic restorative compositions, said instrument comprising:
    a handle;
    a shaft extending from said handle;
    an end of said shaft opposite the handle having a first cylindrical member movably enclosed within a second outer cylindrical member;
    an end portion of the first cylindrical member having attached thereto a third cylindrical member having a radius smaller than the other two cylindrical members;
    wherein said first cylindrical member has a first, retracted position within said second outer cylindrical member such that when the first cylindrical member is in the retracted position, an end of the third cylindrical member is completely disposed within the second cylindrical member and a space exists beyond the end of the first cylinder within the interior of the second cylinder and around the exterior of the third cylinder, said space to be filled with uncured composite which is subsequently cured to form the amount of pre-cured composite and subsequently placed into the cavitation and pressure applied with the instrument in an outward direction, forcing the pre-cured composite against the matrix band to establish interproximal contact with an adjacent tooth.

18. An instrument used to pre-cure an amount of composite into a chosen geometry, said instrument comprising:

a handle;

a shaft extending from said handle;

an end of said shaft opposite the handle having a first member movably enclosed within a second outer member;

an end portion of the first member having attached thereto a third member having a cross-section smaller than a cross-section of the other two members; and wherein said first member has a retracted position within said second, outer member such that when the first member is in the retracted position, an end of the third member is completely disposed within the second member and a space exists beyond the end of the first member within the interior of the second member and around the exterior of the third member, said spaced to be filled with uncured composite which is subsequently cured to form the amount of pre-cured composite.

19. The instrument of claim 18 further comprising a means for positioning the amount of pre-cured composite into a vertical opening of a tooth cavitation during filling of the cavitation with light curable plastic restorative compositions, in a manner to expand a matrix band outwardly from said vertical opening.

* * * * *